United States Patent [19]
Layman, Jr. et al.

[11] Patent Number: 5,550,285

[45] Date of Patent: Aug. 27, 1996

[54] METHOD FOR PRODUCING CALCIUM SALTS OF [S,S]-ETHYLENEDIAMINE-N,N'-DISUCCINIC ACID

[76] Inventors: William J. Layman, Jr., 15732 Woodmoss Dr.; Kannappan Chockalingam, 11888 Longridge Ave., both of Baton Rouge, La. 70816; Jean-Pierre Lecouvé, 12, avenue Roger Salengro, 68100 Mulhouse, France

[21] Appl. No.: 272,455

[22] Filed: Jul. 11, 1994

[51] Int. Cl.$^6$ ................................................. C07C 229/00
[52] U.S. Cl. .................................................................. 562/565
[58] Field of Search ............................................. 562/565

[56] References Cited

U.S. PATENT DOCUMENTS 3,158,635  11/1964  Kezerian et al. ..................... 260/429
4,704,233  11/1987  Hartman et al. ....................... 252/527

FOREIGN PATENT DOCUMENTS 558905  8/1977  U.S.S.R. .

OTHER PUBLICATIONS

Wagner, "Synthetic Organic Chemistry," pp. 666–670 & 715–727 (1953).

Neal, et al., "Stereospecific Ligands and Their Complexes. I. A Cobalt(III) Complex of Ethylenediaminedisuccinic Acid[1]", *Journal of Inorganic Chemistry*, vol. 7, No. 11, Nov., 1958, pp. 2405–2412.

*Primary Examiner*—Michael L. Shippen
*Attorney, Agent, or Firm*—E. E. Spielman, Jr.

[57] ABSTRACT

This invention relates to a process for the production of a solid calcium [S,S]-ethylenediamine-N,N'-disuccinate by the reaction of calcium aspartate and dihaloethane in an aqueous solvent.

14 Claims, No Drawings

METHOD FOR PRODUCING CALCIUM SALTS OF [S,S]-ETHYLENEDIAMINE-N,N'-DISUCCINIC ACID

BACKGROUND OF THE INVENTION

This invention relates to a method for the production of solid calcium salts of [S,S]-ethylenediamine-N,N'-disuccinic acid.

Ethylenediamine-N,N'-disuccinic acid (EDDS) and its various alkali metal, alkaline earth metal, ammonium and substituted ammonium salts are well recognized by the detergent industry as useful chelating agents in cleaning formulations. (See U.S. Pat. No. 4,704,233, which is incorporated herein by reference as if fully set forth.) These salts and acids are theorized to chelate metals such as iron, manganese, copper and other multivalent metal ions. The metal ions are constituents of certain organic stains or act to stabilize such stains when present in washing solutions. Besides providing for the chelating function, EDDS and its salts are non-phosphorous compounds and, as a result, are environmentally desirable. Even further, EDDS and its salts exhibit biodegradability. The degree of biodegradability depends upon the optical EDDS isomer involved. Of the three optical isomers, [R,R], [R,S] and [S,S], the [S,S] isomer is most easily biodegradable and is thus preferred.

The [S,S] isomer can be synthesized from L-aspartic acid, generally as the salt, and 1,2-dibromoethane. See for example, the synthesis of [S,S] EDDS from sodium L-aspartate and 1,2-dibromoethane which is reported in Neal and Rose, *Stereospecific Ligands and Their Complexes of Ethylenediamine-disuccinic Acid, Inorganic Chemistry*, Vol. 7. (1968), pp. 2405–2412. In this synthesis, sodium L-aspartate is reacted with 1,2dibromoethane in a basic aqueous medium. The resultant sodium salt of [S,S] EDDS is soluble in the reaction system and, absent evaporation techniques, is not directly recoverable therefrom as a solid. According to Neal and Rose, the EDDS can be recovered from the solution by slowly acidifying the solution through the addition of concentrated hydrochloric acid to obtain a solution pH of 3.5. The acidification converts the [S,S]-EDDS salt to its acid, which acid crystallizes and precipitates from the solution. Fine crystals are said to precipitate out as the pH moves between pH 7 and 3.5. To purify the EDDS precipitate, which is contaminated with co-precipitates, the solids are recovered and redissolved in a NaOH solution followed by reacidification. The cycle is repeated two times. The final precipitate is washed with water to remove HCl and any traces of L-aspartic acid. While it is implied by Neal and Rose that this purification procedure yields a pure product, the procedure is burdened in terms of procedure time and in terms of HCl utilization due to the multi-cycle purification train.

THE INVENTION

This invention relates to a process for the preparation of solid calcium salt of [S,S] EDDS which is directly recoverable from the reaction of calcium L-aspartate and 1,2-dihaloethane. The obtainment of the solid salts is particularly advantageous as the producers of cleaning formulations will have a choice of using the salt in the solid form or in the liquid form. The liquid form can be easily obtained by simply dissolving the solid salt in a solvent, e.g., water, which has an acidic pH sufficient to effect such dissolution.

The process comprises: dissolving 1,2-dihaloethane into an aqueous calcium L-aspartate solution, which solution has a pH within the range of from about 9 to about 14; forming calcium [S,S]-ethylenediamine-N,N'-disuccinate by the reaction of calcium L-aspartate and 1,2-dihaloethane in the solution; and precipitating the formed calcium [S,S]-ethylenediamine-N,N'-disuccinate from the solution at a solution pH which is within the range of from about 9 and to about 11. During the reaction of calcium L-aspartate and 1,2-dihaloethane, it is preferred that the molar concentration of the calcium L-aspartate in the solution be within the range of from about 0.3 to about 2.0 moles of the aspartate per liter of the solution.

The calcium aspartate solution used in the process of this invention can be obtained by the reaction, in an aqueous solvent, of L-aspartic acid and basic calcium salt. The amount of calcium salt used is that amount which is needed to give the solution the desired pH and calcium aspartate concentration. The basic calcium salt can be any calcium salt capable of producing a calcium aspartate solution meeting the above recited concentration and pH ranges, provided that the salt anion does not interfere with the obtainment of the solid calcium salt of [S,S] EDDS in accordance with this invention. The basic calcium salt is preferably $CaCO_3$, $Ca(OH)_2$, $CaO$ or mixtures of two or more of the foregoing. Especially preferred is $Ca(OH)_2$.

While the forgoing recites a preferred manufacturing route for the calcium aspartate solution, it is to be understood that other routes are suitable provided that such routes do not introduce solution constituents which would be harmful in the production of the desired solid calcium [S,S] EDDS salt.

Generally, the calcium aspartate salt in solution will be the dicarboxylate salt and can be represented by the structure,

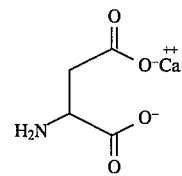

Other calcium salts are possible, for example,

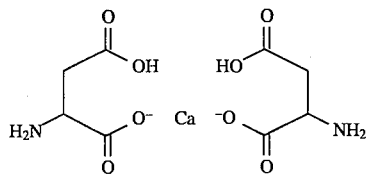

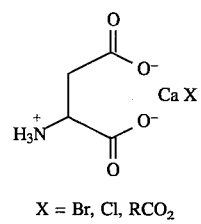

X = Br, Cl, $RCO_2$

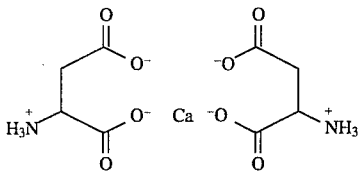

Non-calcium cations may be present in the calcium aspartate solution. The non-calcium cations include the alkali metal, non-calcium alkaline earth metal, ammonium, substituted ammonium cations and mixtures of two or more of the foregoing. The only proviso is that these cations cannot be present to such an extent that their presence or the presence of their reaction products will adversely affect the use of the calcium aspartate solution in the production of the calcium [S,S] EDDS salt.

When non-calcium cations are present in the solution, several salts are possible, i.e.,

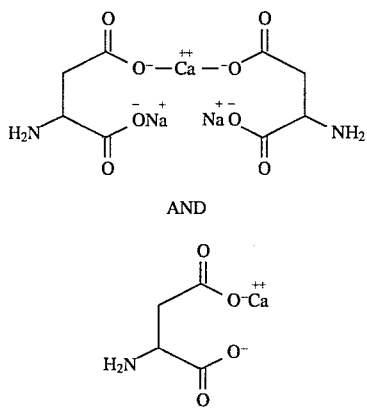

As before stated, the calcium aspartate solution should contain from about 0.2 to about 2.0 moles of calcium aspartate per L of solution. Concentrations outside of the low end of the range are not preferred as the calcium aspartate/dihaloethane reaction rate will be too slow for commercial purposes. Concentrations in excess of the upper end of the range can be problematical as such concentrations could cause the dihaloethane used in the calcium [S,S] EDDS salt reaction to "salt out" of the solution, i.e., be rendered immiscible in the solution, and thus not be available for reaction. Also, higher concentrations of calcium aspartate result in higher concentrations of the aspartate in the precipitated Ca EDDS salt and, therefore, require more rigorous washing of the Ca EDDS precipitate. A preferred calcium aspartate concentration is within the range of from about 0.5 to about 1.5 moles calcium aspartate per L of solution.

In those cases where there are non-calcium salts present in the solution, care must be taken so that the concentration of these salts, when coupled with the calcium salt concentration, will not result in the salting out of dihaloethane.

The aqueous solvent constituent of the calcium aspartate solution is at least 50 vol % water. For most cases, the preferred solvent is water. Water-alkanol solutions can be beneficial if there is a problem with keeping the dihaloethane in solution. Care must be taken, however, since small amounts of alkanol, say 15 vol %, can greatly reduce the solubility of the calcium aspartate reactant. Thus, the alkanol presence is preferably below 15 vol % and, most preferably, less than 5 vol % as they aid in solubilizing the dihaloethane without practical impact on the solubility of the calcium aspartate.

The 1,2-dihaloethane used in the process of this invention is preferably dichloroethane, dibromoethane or a mixture thereof. When dichloroethane is used, the reaction temperature should be within the range of from about 90 to about 120° C. and when dibromoethane is used the reaction temperature should be within the range of from about 75 to about 95° C. and most preferably within the range of from about 80 to about 90° C. The most preferred dihaloethane is dibromoethane. When a mixture of dichloro- and dibromoethane is used, the reaction temperature should be below the upper end of the dichloroethane range and above the lower end of the dibromoethane range.

When 1,2-dichloroethane is used, the reaction pressure should be superatmospheric to prevent volatilization of the 1,2-dichloroethane. The reaction pressure when using 1,2-dibromoethane can be atmospheric or slightly less due to the higher boiling point of 1,2-dibromoethane.

The calcium aspartate solution's pH and calcium aspartate concentration are two parameters which should be controlled during the reaction of the calcium aspartate and dihaloethane. The pH of the solution should be within the range of from about 9 to about 14. Preferably, the pH should be within the range of from about 9.5 and about 11. Most preferred is a pH range of from about 10.0 and 10.5. The pH of the solution can be conveniently measured by use of a conventional pH meter, such as those made by Fischer Scientific Corporation, with the meter probe being placed in contact with the solution. The foregoing pH values are within a ±0.03 range. Since pH is important to the process of this invention, it is preferred to measure the pH values by taking a sample of the solution, diluting it: 20:1 with water and then measuring the pH of the diluted sample. With dilution, a more accurate value can be obtained.

As the calcium aspartate and 1,2-dihaloethane react, calcium [S,S] EDDS salt is formed. It has been learned that good precipitation of the calcium [S,S] EDDS salt occurs when the solution is at a pH within the range of from about 9.0 and about 11 and preferably between 9.5 and 10.5. Optimum precipitation is expected at a pH within the range of from about 10.0 and 10.5. The pH of the system is preferably maintained within these preferred ranges throughout the reaction of the dihaloethane and calcium aspartate. While it is desirable to have such continued maintenance, it is not necessary. It is possible to let the pH drift within the larger pH range (9.0 to 14) during the reaction period and to then bring the solution pH to a value which is within the preferred ranges for the precipitation of the calcium [S,S] EDDS salt.

In addition to the formation of the calcium [S,S] EDDS salt precipitate, hydrogen halide will also be produced. Without the addition of a base to the solution, its pH would drop. To control the pH within the above-recited ranges, base is added as needed. Suitable bases are those which can raise the pH and which do not adversely affect the reaction or solution. Preferred are basic calcium salts, such as $Ca(OH)_2$. Most preferred are calcium aspartate solutions having a pH of about 12–13.

It is important to understand that the control of the solution pH can be deteriorated if the dihaloethane feed rate to the calcium aspartate solution is too fast. If the dihaloethane is added all at once or at too fast a rate, the amount of hydrogen halide produced can overwhelm the ability of the solution's own buffering capacity and the base's neutralizing ability to keep the pH within the desired range. Thus, the dihaloethane feed rate should be moderated. The best dihaloethane feed rate will be influenced by the scale and configuration of each reaction system. Thus, empirical testing will identify the best feed rate. See Example 1 for an exemplary feed rate.

In addition to the solution pH, the calcium aspartate concentration of the solution should be kept within the before-recited range during the reaction. The calcium aspartate concentration, if not provided for, will naturally drop over the reaction period as it is consumed by its reaction with the dihaloethane. To keep the concentration within the range, make-up calcium aspartate is added, as needed, to the solution. As the reaction proceeds, the excess calcium aspartate in solution acts to buffer against excessive pH changes.

It has been found that with pH and calcium aspartate concentration maintenance, an easily filterable or centrifugable calcium [S,S] EDDS salt is obtained. It is theorized that by using effective pH control and by closely maintaining the calcium aspartate concentration, the system is in equilibrium and the crystal growth of the EDDS salt is controlled. Controlled growth results in the formation of large crystals of the [S,S] EDDS salts. The production of EDDS salt fines is also reduced as supersaturation conditions are avoided. Seeding the reaction with a heel will also promote formation of larger crystals.

It is convenient if the base and the makeup-calcium aspartate are added to the solution together as a thick concentrated slurry. The calcium aspartate would be in the form of an aqueous solution and crystals while the base would be a solid.

The formed calcium [S,S] EDDS salt precipitate can be easily recovered from the reaction solution by use of conventional liquid-solid separation techniques, such as filtration, centrifugation, etc. The recovered precipitate is preferably washed with water to reduce impurity levels, the main impurities being calcium aspartate, calcium halide, calcium salt of [R,S] EDDS, and the calcium salt of hydroxy ethyl aspartic acid. These impurities, or light ends, generally do not exceed 5.0 wt %. Another feature of this invention is that the produced precipitate contains very little calcium aspartate or precipitated aspartic acid. For example, a precipitate wet cake of this invention would contain typically 41 wt %, e.g., from about 35 to about 49 wt %, solid calcium [S,S] EDDS salt and typically about 3.5 wt %, e.g., 1.5 to 6.0 wt % L-aspartic acid, the balance of the wet cake is substantially all water.

An advantage offered by solid calcium [S,S] EDDS salts is that they are easily convertible to [S,S] EDDS and to various non-calcium [S,S] EDDS salts. The conversion to the acid is accomplished by titrating the calcium salt with a mineral acid such as HCl. The recovered [S,S] EDDS can be used as a chelating agent itself or it can be converted to a non-calcium salt by neutralization with a non-calcium basic salt, such as NaOH.

An important advantage of the process of this invention is that the filtrate, which is comprised of 14–20% calcium aspartate, 5–18% calcium halide, 1.8–3.6 wt % calcium EDDS, can be directly used as a feed to a subsequent reaction. Additional calcium aspartate is added, as needed, to obtain the desired calcium aspartate concentration. Also, the level of calcium aspartate can be reduced to less than 1 wt % if the Ca EDDS is reslurried in water.

EXAMPLE I

Fresh Reaction

A 2000-ml, indented, three-neck, round-bottom flask was equipped with an overhead stirrer, Claisen adapter and thermometer. The flask was then charged with 0.7 mole of L-aspartic acid, 0.63 mole of calcium hydroxide, and 623 g of $H_2O$. The solution was heated to 90° C. under positive nitrogen pressure. Meanwhile, 1.4 mole of L-aspartic acid, 1.81 mole of calcium hydroxide and 560 g of $H_2O$, were combined in a 1000 ml round-bottom flask equipped with an over-head stirrer. This slurry was fed via peristaltic pump to the reactor over a 6 hour period. Simultaneously, 0.54 mole of EDB was co-fed via syringe pump to the reactor over the same period. Formation of the calcium EDDS precipitate was observed three hours after initiating the co-feed. A 700 ml portion of the slurry was then removed for seeding the next reaction. The remaining slurry was heated for another 2 hours. The reaction slurry was filtered and the resulting wet-cake washed with 80 g of $H_2O$. The yield of calcium EDDS wet cake was 156 g. Analysis showed that the cake was comprised of 35 wt % calcium [S,S] EDDS, 0.03 wt % calcium [R,S] EDDS and 3.9 wt % calcium aspartate. The filtrate and wash were recycled in the subsequent experiments to produce more calcium EDDS.

EXAMPLE II

1st Recycle

The reaction apparatus was charged with the 700 ml slurry from the fresh reaction. The slurry was heated to 90° C. under positive nitrogen pressure. Meanwhile, 648 g of the filtrate and 32 g of the wash (from the fresh reaction) 0.83 mole of L-aspartic acid and 1.29 mole of calcium hydroxide were combined in a stirred 1000 ml round-bottom flask. This slurry was fed via peristaltic pump to the reactor over a 6.2 hour period. Simultaneously, 0.52 mole of EDB was co-fed via syringe pump to the reactor over 5.67 hour. The reaction mixture was heated for an additional 2 hours and a 410 ml portion of the slurry was removed. The remaining slurry was heated for an additional hour and then cooled. The reaction slurry was filtered and the resulting wet-cake washed with 200 g of $H_2O$. The yield of calcium EDDS wet cake was 299.17 g. Analysis showed that the cake was comprised of 39 wt % calcium [S,S] EDDS, 0.06 wt % calcium [R,S] EDDS and 3.4 wt % calcium aspartate. Again the wash and filtrate were kept separate and recycled to produce more calcium EDDS. A 264 g portion of the filtrate was acidified with concentrated HCl and then filtered to recover aspartic acid and EDDS for recycle.

EXAMPLE III

2nd Recycle

The reaction apparatus was charged with the 410 ml slurry removed from the first recycle. The slurry was heated to 90° C. under positive nitrogen pressure. Meanwhile, 612 g of the filtrate and 307 g of the wash from the first recycle, 82.6 g of wash from the fresh reaction, 1.1 mole of L-aspartic acid, 1.4 mole of calcium hydroxide and 40 g $H_2O$ were combined in a 2000 ml round-bottom flask equipped with an overhead stirrer. This slurry was fed via peristaltic pump to the reactor over a 6.25 hour period. Simultaneously, 0.53 mole of EDB was fed via syringe pump to the reactor over 6.2 hours. The reaction mixture was heated for an additional 2 hours and a 410 ml portion of the slurry was removed. The remaining slurry was heated for an additional hour and then filtered. The resulting wet cake was washed with 189 g of $H_2O$. The yield of calcium EDDS wet cake was 293.17 g. Analysis showed that the cake was comprised of 41 wt % calcium [S,S] EDDS, 0.06 wt % calcium [R,S] EDDS and 1.5 wt % calcium aspartate. Again the wash and filtrate were kept separate and recycled to produce more calcium EDDS. A 464 g portion of the filtrate was acidified with concentrated HCl and then filtered to recover aspartic acid and EDDS to be recycled.

EXAMPLE IV

3rd Recycle

The reaction apparatus was charged with the 410 ml slurry removed from the second recycle. The slurry was heated to 90° C. under positive nitrogen pressure. Meanwhile, 496 g of the filtrate and 260 g of the wash from the second recycle, 233.7 g of recovered L-aspartic acid wet cake (0.47 mole of contained aspartic acid, obtained from the first and second recycle experiments), 0.87 mole of L-aspartic acid, 1.38 mole of calcium hydroxide and 100 g $H_2O$ were combined in the stirred 2000 ml round-bottom flask. This slurry was fed via peristaltic pump to the reactor over a 6.2 hour period. Simultaneously, 0.54 mole of EDB was co-fed via syringe pump to the reactor over 6.1 hours. The reaction mixture was heated for an additional 2 hours and a 200 ml portion of the slurry was removed. The remaining slurry was heated for an additional 2 hours and then filtered. The resulting wet cake was washed with 178 g of $H_2O$. The yield of calcium EDDS wet cake was 322.9 g. Analysis showed that the cake was comprised of 43 wt % calcium [S,S] EDDS, 0.2 wt % calcium [R,S] EDDS and 6.0 wt % calcium aspartate. Again the wash and filtrate were kept separate and recycled to produce more calcium EDDS. A 884 g portion of the filtrate was acidified with concentrated HCl and then filtered to recover aspartic acid and EDDS to be recycled.

EXAMPLE V

4th Recycle

The reaction apparatus was charged with the 200 ml slurry removed from the third recycle. The slurry was heated to 90° C. under positive nitrogen pressure. Meanwhile, 395.8 g of the filtrate and 228 g of the wash from the third recycle, 263 g of recovered L-aspartic acid (L-aspartic acid content 0.55 mole obtained from the third recycle experiment), 0.91 mole of calcium hydroxide and 50 g $H_2O$ were combined in a 2000 ml round-bottom flask. This slurry was fed via peristaltic pump to the reactor over a 6.5 hour period. Simultaneously, 0.46 mole of EDB was fed via syringe pump to the reactor over 6.0 hours. The reaction mixture was heated for 12 hours and then filtered. The resulting wet cake was washed with 260 g of $H_2O$. The yield of calcium EDDS wet cake was 251.0 g. Analysis showed that the cake was comprised of 49 wt % calcium [S,S] EDDS, 0.2 wt % calcium [R,S] EDDS and 3.4 wt % calcium L-aspartate. The wash and filtrate were combined, acidified with acid and filtered to yield a wet cake that contained 0.40 mole of L-aspartic acid and 0.06 mole of [SS] EDDS.

As can be seen from the foregoing Examples, the process of this invention provides for the production of a solid calcium [S,S] EDDS salt which is recoverable from the reaction system by a simple filtration step. There is no need for the reacidification and redissolution cycles of the Neal and Rose process.

What is claimed:

1. A process for producing solid calcium [S,S]-ethylenediamine-N,N'-disuccinate, which process comprises: providing a solution which includes calcium L-aspartate, 1,2-dihaloethane and an aqueous solvent and which has a pH within the range of from about 9 to about 14; forming calcium [S,S]-ethylenediamine-N,N'-disuccinate by the reaction of calcium L-aspartate and 1,2-dihaloethane in the solution; and precipitating the formed calcium [S,S]-ethylenediamine-N,N'-disuccinate from the solution at a solution pH which is within the range of from about 9.0 and to about 11.

2. The process of claim 1 wherein during formation of calcium [S,S]-ethylenediamine-N,N'-disuccinate, the calcium aspartate in the solution is within the range of from about 0.3 to about 2.0 moles of calcium aspartate per liter of the solution.

3. The process of claim 1 wherein precipitation of calcium [S,S]-ethylenediamine-N,N'-disuccinate occurs with the solution pH being within the range of from about 9.5 to about 10.5.

4. The process of claim 2 wherein precipitation of calcium [S,S]-ethylenediamine-N,N'-disuccinate occurs with the solution pH being within the range of from about 10.0 to about 10.5.

5. The process of claim 1 wherein the solution pH is at least partially controlled during the reaction of dihaloethane and calcium aspartate by monitoring the solution pH and by adding, to the solution, an amount of calcium base which is needed to keep the solution pH within the selected pH range.

6. The process of claim 2 wherein the calcium aspartate concentration is monitored during the reaction of dihaloethane and calcium aspartate and is maintained within the range of from about 0.3 to about 2.0 moles of calcium aspartate per liter of the solution by the addition of calcium aspartate to the solution as is needed.

7. The process of claim 6 wherein the solution pH is at least partially controlled during the reaction of dihaloethane and calcium aspartate by monitoring the solution pH and by adding, to the solution, an amount of calcium base which is needed to keep the solution pH within the selected pH range.

8. The process of claim 5 wherein the solution pH is controlled additionally by adding the dihaloethane to the solution at a rate which insures that the amount of hydrogen halide generated by the reaction of dihaloethane and calcium aspartate is not so great as to overcome the ability to control the solution pH by the addition of base to the system.

9. The process of claim 8 wherein the calcium aspartate concentration is monitored during the reaction of dihaloethane and calcium aspartate and is maintained within the range of from about 0.3 to about 2.0 moles of calcium aspartate per liter of the solution by the addition of calcium aspartate to the solution as is needed.

10. The process of claim 1 wherein the dihaloethane is 1,2-dibromoethane.

11. The process of claim 5 wherein the calcium base is $Ca(OH)_2$.

12. The process of claim 9 wherein the calcium aspartate and calcium base are added together as an aqueous slurry.

13. The process of claim 9 wherein the dihaloethane is 1,2-dibromoethane and the calcium base is $Ca(OH)_2$.

14. The process of claim 1 wherein the calcium [S,S]-ethylenediamine-N,N'-disuccinate precipitate is recovered from the solution and the resultant solution is then used as a feed to a second process which comprises: forming a reaction mass to include calcium L-aspartate, 1,2-dihaloethane and an aqueous solvent and which has a pH within the range of from about 9 to about 14; obtaining calcium [S,S]-ethylenediamine-N,N'-disuccinate by the reaction of calcium L-aspartate and 1,2-dihaloethane in the solution; and precipitating the formed calcium [S,S]-ethylenediamine-N,N'-disuccinate from the solution at a solution pH which is within the range from about 9.0 and to about 11.

* * * * *